United States Patent [19]

Cesa et al.

[11] Patent Number: 4,847,411
[45] Date of Patent: Jul. 11, 1989

[54] 1,6-HEXANEDIAMIDES FROM 3-PENTENAMIDES

[75] Inventors: Mark C. Cesa, South Euclid; Robert A. Dubbert, Solon; James D. Burrington, Richmond Heights, all of Ohio

[73] Assignee: The Standard Oil Company, Cleveland, Ohio

[21] Appl. No.: 730,219

[22] Filed: May 3, 1985

[51] Int. Cl.$^4$ .................. C07B 43/06; C07C 103/147
[52] U.S. Cl. ..................................... 564/132; 548/552
[58] Field of Search ........................................ 564/132

[56] References Cited

U.S. PATENT DOCUMENTS

| | | | |
|---|---|---|---|
| 2,542,766 | 2/1951 | Gresham | 564/132 |
| 4,331,612 | 5/1982 | Pesa et al. | 564/132 |

Primary Examiner—Charles F. Warren
Assistant Examiner—Carolyn S. Greason
Attorney, Agent, or Firm—C. S. Lynch; D. J. Untener; L. W. Evans

[57] ABSTRACT

A process for making a diamide of the formula

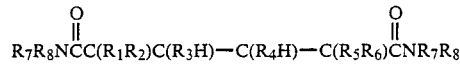

by reacting a monoamide compound of the formula

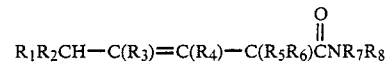

with CO and an amine or ammonia of the formula $R_7R_8NH$ in the liquid phase under essentially anhydrous conditions at a temperature in the range from 120° to 210° C., where each of $R_1$, $R_2$, $R_3$, $R_4$, $R_5$, $R_6$, $R_7$ and $R_8$ is selected independently from H and a $C_1$ to $C_{12}$ hydrocarbyl containing no ethylenic or acetylenic unsaturation.

5 Claims, No Drawings

1,6-HEXANEDIAMIDES FROM 3-PENTENAMIDES

This is a continuation of application Ser. No. 772,028, filed Sept. 3, 1985, now abandoned.

This application is a continuation-in-part of U.S. Ser. No. 685,656, filed Dec. 24, 1984, which is a continuation of U.S. Ser. No. 676,364, filed Nov. 29, 1984.

In an important aspect this invention relates to a new method of making adipamide or derivatives thereof by the hydrocarbamylation of 3-pentenamide or derivatives thereof.

Adipamide is currently prepared from adiponitrile by controlled hydrolysis. The adiponitrile for the hydrolysis is prepared commercially by electrohydrodimerization of acrylonitrile or by hydrocyanation of 1,3-butadiene.

It is an object of the present invention to provide a new and improved method of making adipamide or derivatives thereof.

It is a further object of the invention to provide a relatively simplified method of making adipamide from 3-pentenamide.

Other objects, as well as aspects, features and advantages, of the invention will become apparent from a study of the specification, including the claims.

The foregoing and other objects are accomplished by the present invention according to which there is provided a process for making a diamide of the formula

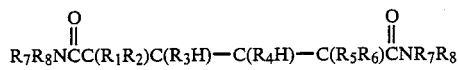

by reacting a compound of the formula

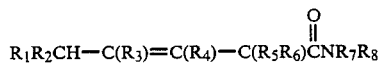

with CO and an amine or ammonia of the formula $R_7R_8NH$ in the liquid phase under essentially anhydrous conditions at a temperature in the range from 120° to 210° C., where each of $R_1$, $R_2$, $R_3$, $R_4$, $R_5$, $R_6$, $R_7$ and $R_8$ is selected independently from H and a $C_1$ to $C_{12}$ hydrocarbyl containing no ethylenic or acetylenic unsaturation.

In the usual practice of the invention the compound $R_7R_8NH$ is $NH_3$. Especially useful starting material amides are the 3-alkene amides, i.e. where $R_1$, $R_2$, $R_3$, $R_4$, $R_5$, $R_6$, $R_7$ and $R_8$ are all alkyl groups or H, particularly those 3-alkene amides having 5 to 17 carbon atoms, and in particular 3-pentenamide.

The usual CO pressure used at reaction temperature is in the range from 500 to 10,000 psig. Usual reaction times are from 5 to 50 hours.

We believe that the reaction of a substituted or unsubstituted 3-pentenamide with CO and ammonia or a primary or a secondary amine to make a substituted or unsubstituted 1,6-hexanediamides is a reaction entirely undisclosed in the prior art, with or without a catalyst, and we believe that this reaction per se is new and unobvious, broadly. In carrying out this reaction, however, we have found a catalyst to be necessary.

One class of such catalysts has the formula

where M is one or more of a Group VIII metal, Mn and Re; L is one or more of $R_3P$, $R_2S$, $R_2Se$, $R_3N$, $R_3As$, $R_3Bi$, $R_3Sb$, $R_2Sn$ and $R_4Sn$, where R is selected from H, or alkyl, aryl, alkoxy, aryloxy, dialkylamido, diarylamido, alkylsulfido, and arylsulfido containing 1-30 carbon atoms; X is one or more of F, Cl, Br, I, H, $SnF_3$, $ClO_4$, $HCO_3$ SCN, —NC, NCS, O, S, Se, $SO_4$, $NO_3$, $PO_4$, $SO_3$, $ClO_4$, $HCO_3$ and $CO_3$; m=1-16, n=0-40, l=0-40, and x=0-16, where $n+l+x \geq m$.

In a representative example, a glass-lined stainless steel high pressure bomb reactor containing a magnetic stir bar was charged with 7.28 mole parts 3-pentenamide, 0.271 mole parts $Co_2(CO)_8$, 3.08 mole parts 4-methylpyridine, 2.8 mole parts triphenylphosphine and 52.9 mole parts $NH_3$, and 0.2 mole parts hexadecane internal standard in 195 mole parts of tetrahydrofuran solvent. Then CO was added to a pressure of 2200 psig, and the bomb was sealed and the reaction mixture stirred at 200° C. for 18 hours, then cooled to room temperature. The pressure was then released and the reaction mixture was analyzed by gas chromatography. Conversion of 3-pentenamide was 100 percent. Yield of adipamide was 2.6 percent and the yield of 5-methylpyrrolidone was 9.28 percent.

The products of the invention are useful to make the corresponding diamines by known methods, and such diamines are useful to make nylon polyamide high polymer plastics well known methods.

As will be evident to those skilled in the art, modifications of this invention can be made or followed in the light of the foregoing disclosure without departing from the spirit and scope of the disclosure or from the scope of the claims.

We claim:

1. A process for making a diamide of the formula

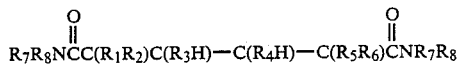

by reacting a monoamide compound of the formula

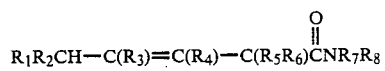

with CO and an amine or ammonia of the formula $R_7R_8NH$ in the liquid phase under essentially anhydrous conditions at a temperature in the range from 120° to 210° C., where each of $R_1$, $R_2$, $R_3$, $R_4$, $R_5$, $R_6$, $R_7$ and $R_8$ is selected independently from H and a $C_1$ to $C_{12}$ hydrocarbyl containing no ethylenic or acetylenic unsaturation.

2. A process of claim 1 where $R_7$ and $R_8$ are H.

3. A process of claim 1 where $R_7$ and $R_8$ are H and the monoamide is 3-pentenamide.

4. A process of claim 1 where $R_7$ and $R_8$ are H wherein each of $R_1$, $R_2$, $R_3$, $R_4$, $R_5$, $R_6$, $R_7$ and $R_8$ is an alkyl group or H.

5. A process of claim 5 wherein the said monoamide has 5-17 carbon atoms.